United States Patent [19]

Williamitis et al.

[11] Patent Number: 5,773,081

[45] Date of Patent: Jun. 30, 1998

[54] METHOD FOR COATING OF OBJECTS USING A ROTATING RESILIENT MATRIX

[75] Inventors: Victor A. Williamitis, Dayton, Ohio; Jeanne E. Lambert, Conyers, Ga.; Min Shiu Lee; Robert A. Taller, both of Sandy, Utah

[73] Assignee: Becton Dickinson and Company, Franklin Lakes, N.J.

[21] Appl. No.: 903,665

[22] Filed: Jul. 31, 1997

Related U.S. Application Data

[63] Continuation of Ser. No. 751,391, Nov. 18, 1996, abandoned, which is a continuation of Ser. No. 509,393, Jul. 31, 1995, abandoned.

[51] Int. Cl.$^6$ ............................................. B05D 1/28
[52] U.S. Cl. ..................... 427/211; 427/428; 427/429; 118/227; 118/244; 118/249; 118/262; 118/264; 118/265
[58] Field of Search .................................. 427/211, 428, 427/429; 118/227, 244, 249, 261, 262, 264, 265, 266

[56] References Cited

U.S. PATENT DOCUMENTS

| 2,870,737 | 1/1959 | Byrnes | 118/227 |
| 4,040,383 | 8/1977 | Vandervort | 118/262 |
| 4,294,187 | 10/1981 | Fogle | 118/264 |
| 4,958,587 | 9/1990 | Fogal et al. | 118/206 |
| 4,963,400 | 10/1990 | Bibbee et al. | 118/227 |
| 5,207,293 | 5/1993 | Eden et al. | 184/101 |

FOREIGN PATENT DOCUMENTS

| 2453682 | 11/1980 | France . |
| 3045950 A1 | 4/1982 | Germany . |
| 4301921 A1 | 8/1993 | Germany . |
| 35-1829 | 3/1960 | Japan . |
| 06 198233 | 11/1994 | Japan . |

OTHER PUBLICATIONS

Patent Abstracts of Japan, vol. 18, No. 553 (C–1263), Oct. 21, 1994.

*Primary Examiner*—Katherine A. Bareford
*Attorney, Agent, or Firm*—Eric M. Lee

[57] ABSTRACT

An apparatus for applying a coating to an object includes a pair of rotating members each including a porous resilient roll mounted for counter-rotatory movement. The members are mounted so that they contact each other during a segment of the movement and are out of contact with each other at other segments of the movement. The apparatus includes a coating supply system for supplying a coating to the resilient rolls. The rotatory movement of the members includes a coating loading segment where the resilient rolls are in physical contact and have a degree of compression with the coating supply system for loading the coating into the rolls. The sequential movement also includes an intermediate segment where the resilient rolls are out of contact with each other and where an object to be coated is movable into position for movement between the resilient rolls when the rolls are in a coating delivery segment. In the coating delivery segment, the resilient rolls are in physical contact and have a degree of compression with each other and with the object to be coated as the object is moved between the rolls. The coating delivery segment serves to apply the coating to the object. A method for applying a coating to an object includes moving an object to be coated between rotating members, each of which includes a porous resilient roll mounted for counter rotatory motion to each other in a coating delivery segment of a sequential movement.

8 Claims, 14 Drawing Sheets

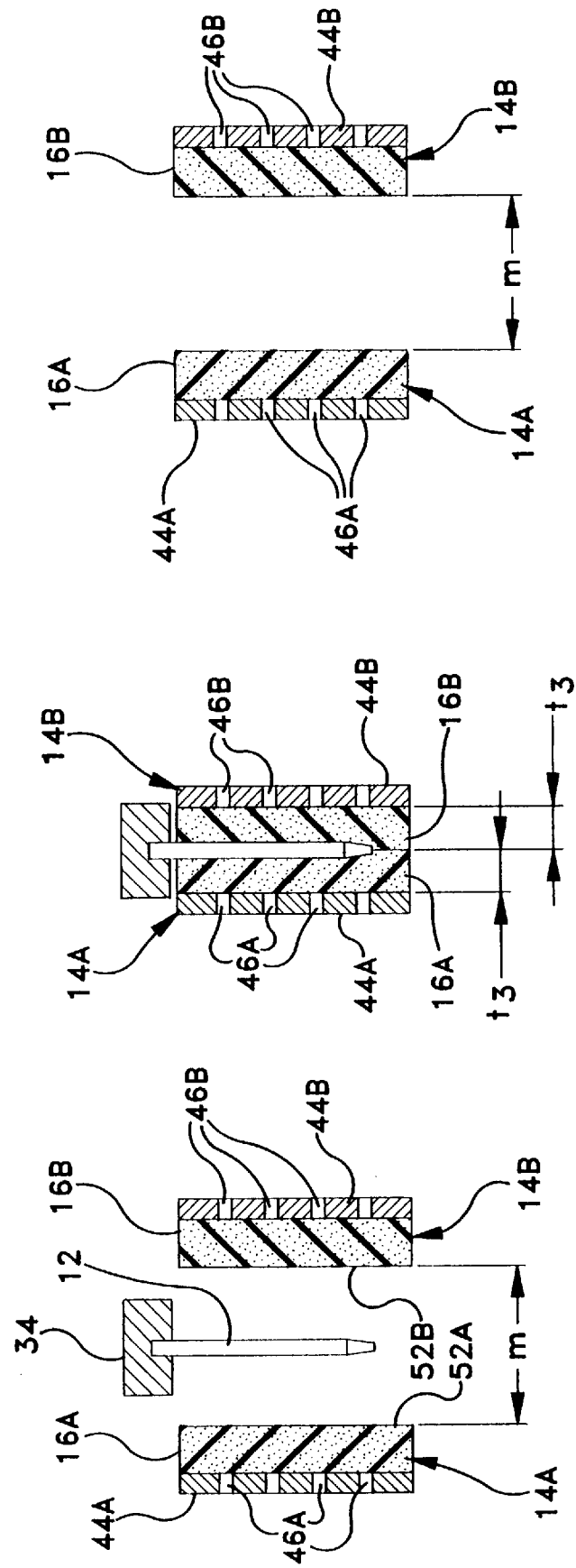

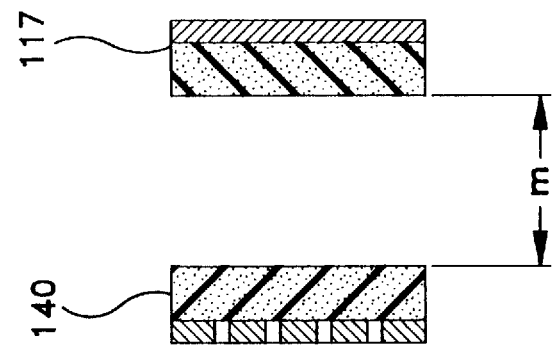
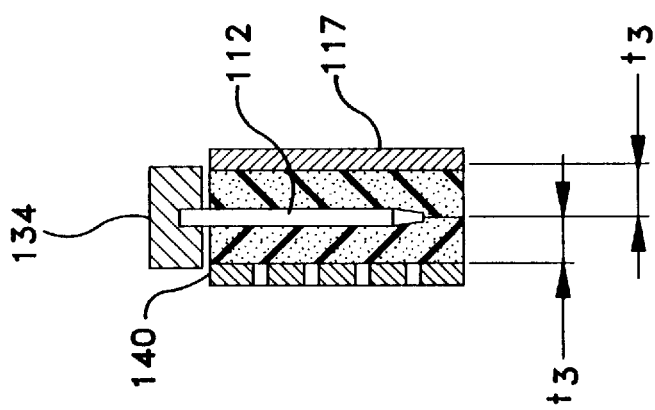
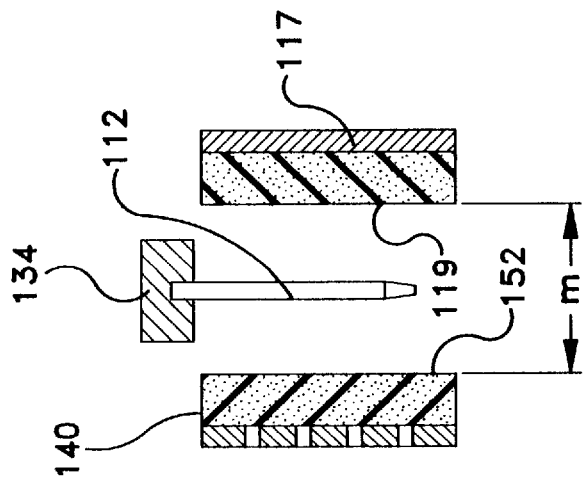

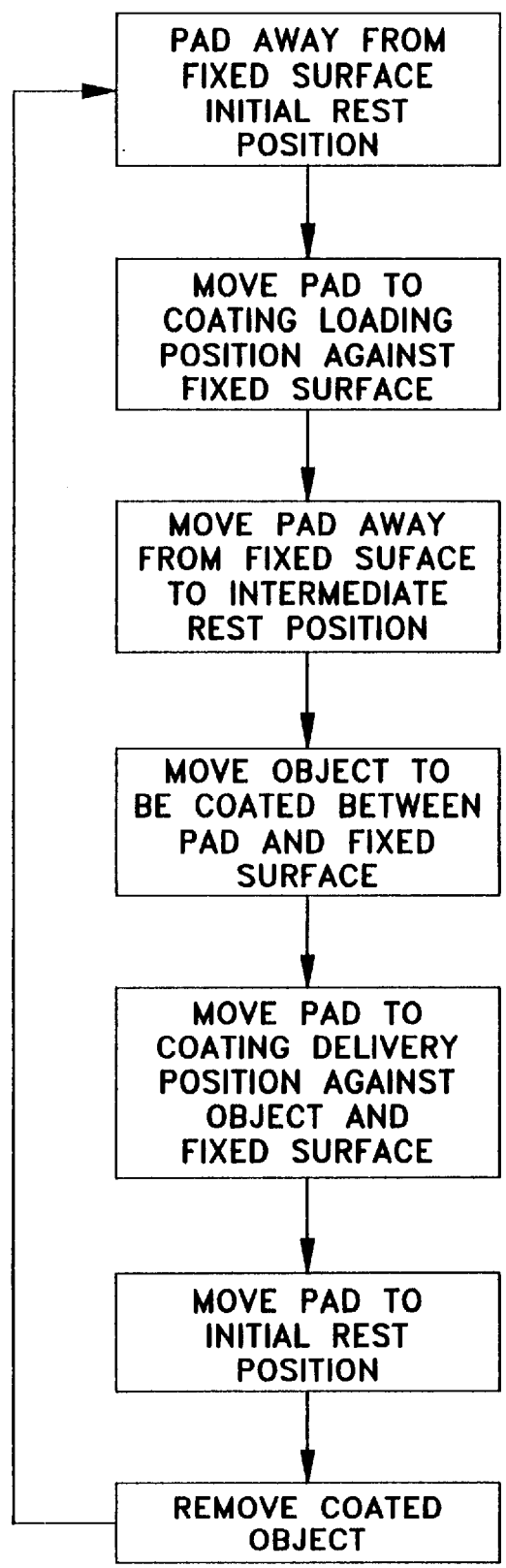

METHOD FOR COATING OF OBJECTS USING A ROTATING RESILIENT MATRIX

This application is a continuation of application Ser. No. 08/1751,391, filed Nov. 18, 1996, now abandoned, which is a continuation of application Ser. No. 08/509,393, filed Jul. 31, 1995 now abandoned.

FIELD OF INVENTION

This invention relates to the coating of objects and more particularly relates to methods and apparatus for applying lubricants to medical devices such as over-the-needle peripheral venous catheters, hypodermic needles, blades and the like.

BACKGROUND OF THE INVENTION

Medical devices are often assembled from components formed from many different materials. It often is necessary to apply a coating of a lubricant to one or more of the components so that a component of one material will readily slide against a component of another material. Examples of this type of application are catheters with guidewires, over-needle catheters, syringe plunger stopper within a syringe barrel, needles for penetration of blood collection tube stoppers and the like. In other medical device applications, a lubricant is applied to a device to ease its penetration into the body. Examples of these applications are surgical blades, hypodermic needles, peripheral venous catheters and the like.

In all of these medical device lubrication applications, there are strict requirements on the amounts of lubricant, the uniformity of the application and a need to avoid contamination of the device with foreign material other than the lubricant. A further requirement on application of lubricant results from the high volume production requirements often resulting in the use of high speed assembly equipment. Thus, any lubricant application must be precise and compatible with high volume production.

Currently, a commonly used lubricant for medical devices is "silicone," i.e. polydimethyl siloxane having a Brookfield viscosity between about 1,000 and 20,000 centistokes (cs). For some applications, the silicone is applied "neat", i.e., without solvent. An example of neat application of silicone to syringe plunger stoppers is disclosed in U.S. Pat. No. 5,207,293 to Eden et al. This patent discloses a method and apparatus for lubricating syringe stoppers by moving the stoppers between a pair of wheels which are positioned partially in a reservoir containing lubricant so that with rotation of the wheels, lubricant is transferred to the stoppers.

Another commonly used neat application method is tumbling a measured quantity of small parts, such as stoppers, with a measured quantity of lubricant so that the parts acquire a coating of the lubricant.

Silicone lubricant also may be sprayed onto the parts either neat or diluted in a carrier solvent. Neat spraying has been found to work well for interior surfaces such as inside syringe barrels. Solvent based dipping or spraying is commonly used for coating hypodermic needles and catheters. Chlorofluorcarbon solvents have proven to be very satisfactory for the delivery of silicone onto medical devices because they are non-toxic, non-flammable, inert, evaporate rapidly without leaving residue and are available in very high purity. Unfortunately, because of the belief that chlorofluorocarbon solvents are responsible for destruction of ozone in the upper atmosphere, most commonly used chlorofluorocarbon solvents will no longer be available. Alternate solvents such as hydrocarbons are flammable, and aqueous based systems generally are not practical for silicones.

Thus, there is a need for an apparatus that is compatible with high production volume and capable of uniformly delivering precise quantities of lubricant to medical devices.

SUMMARY OF THE INVENTION

An apparatus for applying a coating to an object includes a pair of rotating members each including a porous resilient roll mounted for counter-rotatory movement The members are mounted so that they contact each other during a segment of the movement and are out of contact with each other at other segments of the movement. The apparatus includes a coating supply system for supplying a coating to the resilient rolls. The rotatory movement of the members includes a coating loading segment where the resilient rolls are in physical contact and have a degree of compression with the coating supply system for loading the coating into the rolls. The movement includes an intermediate segment where the resilient rolls are out of contact with each other and where an object to be coated is movable into position for movement between the resilient rolls. The movement also includes a coating delivery segment where the resilient rolls are in physical contact and have a degree of compression with each other and with the object to be coated as the object is moved between the rolls. The coating delivery segment serves to apply the coating to the object.

A method for applying a coating to an object includes moving an object to be coated between rotating members each of which includes a porous resilient roll mounted for counter rotatory motion to each other in a coating delivery segment of a sequential movement where the rolls contact each other and the object being coated with a degree of compression. The rolls each have a loading of a coating to be applied to the object.

The apparatus and method of the present invention provide a precise coating of neat lubricant to objects such as hypodermic needles, catheters, guidewires and the like. The invention is compatible with high volume assembly and can be built into a compact station to be fit into existing assembly machinery. The method of the present invention leaves no residual solvent and is simple to practice and maintain.

BRIEF DESCRIPTION OF THE DRAWINGS

FIGS. 2A, 2B, 2C, 2D and 2E are partial cross-section schematic views of the apparatus of FIG. 1 along the line 2—2 showing the reciprocating members in the several positions of a movement sequence;

FIGS. 5A, 5B, 5C, 5D and 5E are partial cross-sectional schematic views of the apparatus of FIG. 4 along the line 5—5 showing the reciprocating member in the several positions of a movement sequence;

FIG. 6 is a flow chart for a method of applying coating to an object with the apparatus of FIG. 4;

DETAILED DESCRIPTION

Figure 1:
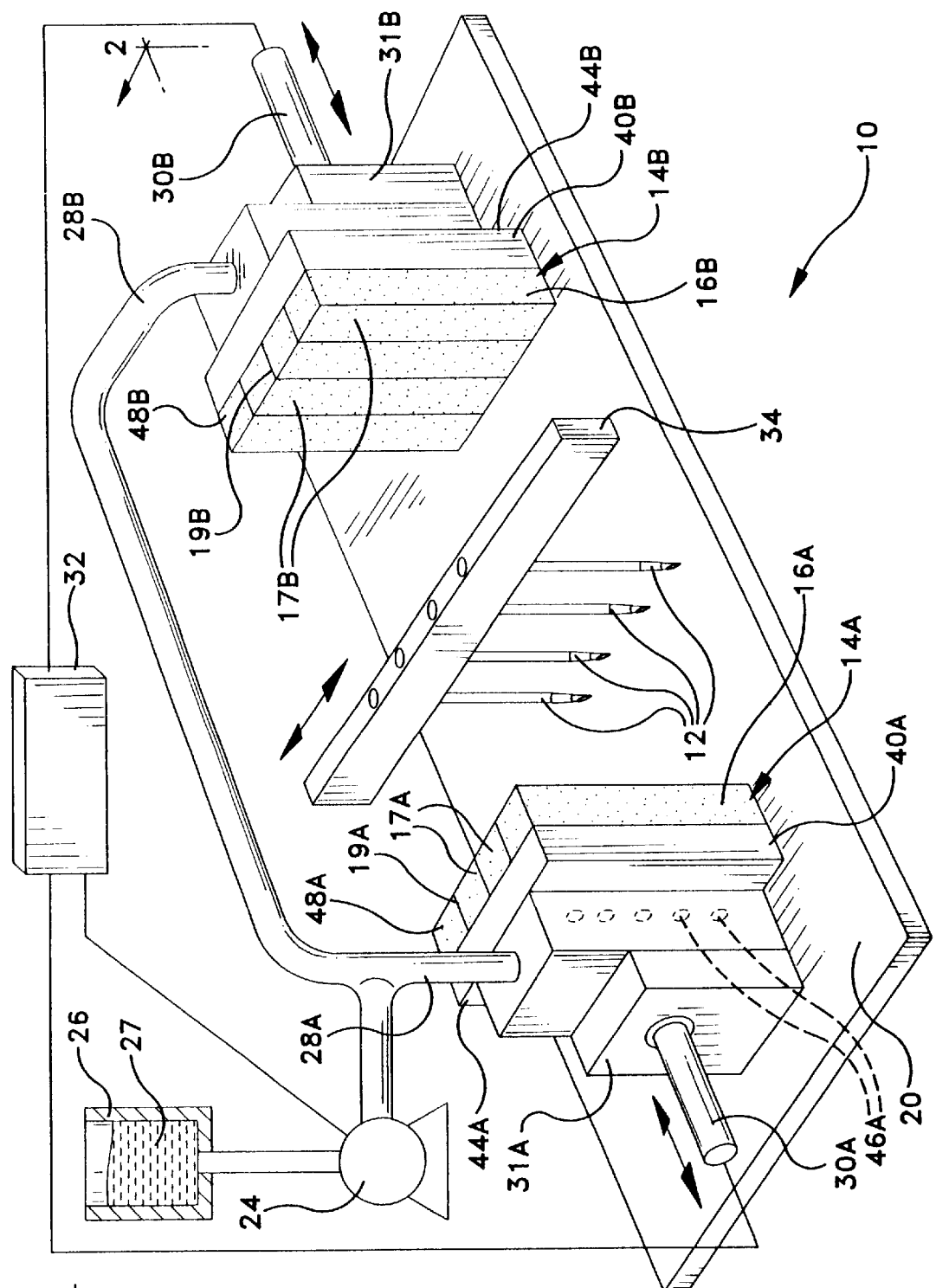
FIG. 1 is a partially sectioned perspective view of the preferred apparatus of the present invention for applying a coating to an object.

While this invention is satisfied by embodiments in many different forms, there is shown in the drawings and is herein be described in detail preferred embodiments of the invention with the understanding that the present disclosure is to be considered exemplary of the principles of the invention and is not considered to limit the invention to the embodiments illustrated. The scope of the invention is measured by the appended claims and their equivalents.

Referring to FIGS. 1 and 2A to 2E, an apparatus 10 for coating an object 12 of the present invention includes a pair of reciprocating members 14A and 14B.

In order to facilitate and simplify the present description, the reciprocating members and other parts of apparatus 10 which are present in pairs are described as symmetrical or identical and are identified with suffixes "A" and "B." For particular applications, such as when object 12 is not symmetrical, the present invention is intended to encompass embodiments where parts of the apparatus herein described in pairs to simplify the description will not be symmetrical or identical.

Reciprocating members 14A and 14B each further include porous resilient pads 16A and 16B. Members 14A and 14B are preferably mounted on a base 20 and include drive mechanisms 30A, 30B, and supports 32A, 32B. Pads 16A, 16B are mounted for movement toward and away from each other.

Apparatus 10 includes a coating supply system 24 for supplying a coating to resilient pads 16A, 16B. Preferably resilient pads 16A, 16B each include backing plates 40A, 40B each having a first side 42A, 42B and a second side 44A, 44B and having a plurality of holes 46A, 46B therethrough. Pads 16A, 16B each further preferably include reticulated elastomeric foam layers 48A, 48B having front sides 52A, 52B and back sides 56A, 56B. Back sides 56A, 56B of preferred foam layer 48A, 48B preferably are fixedly attached to first sides 42A, 42B of the backing plates.

Figure 2B:
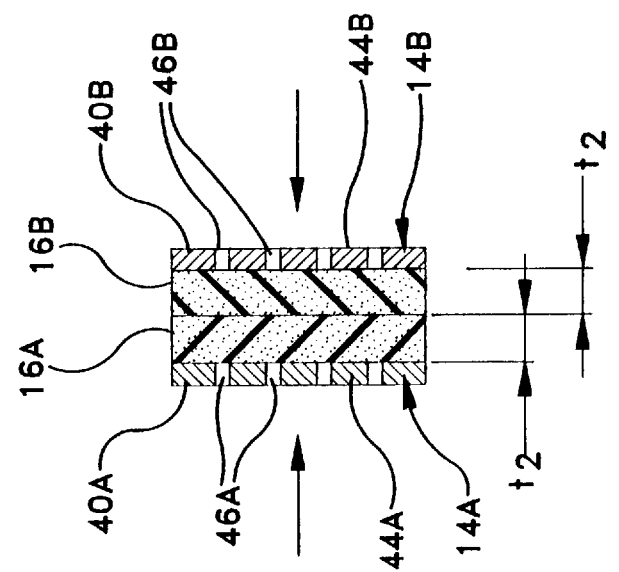
Figure 2A:
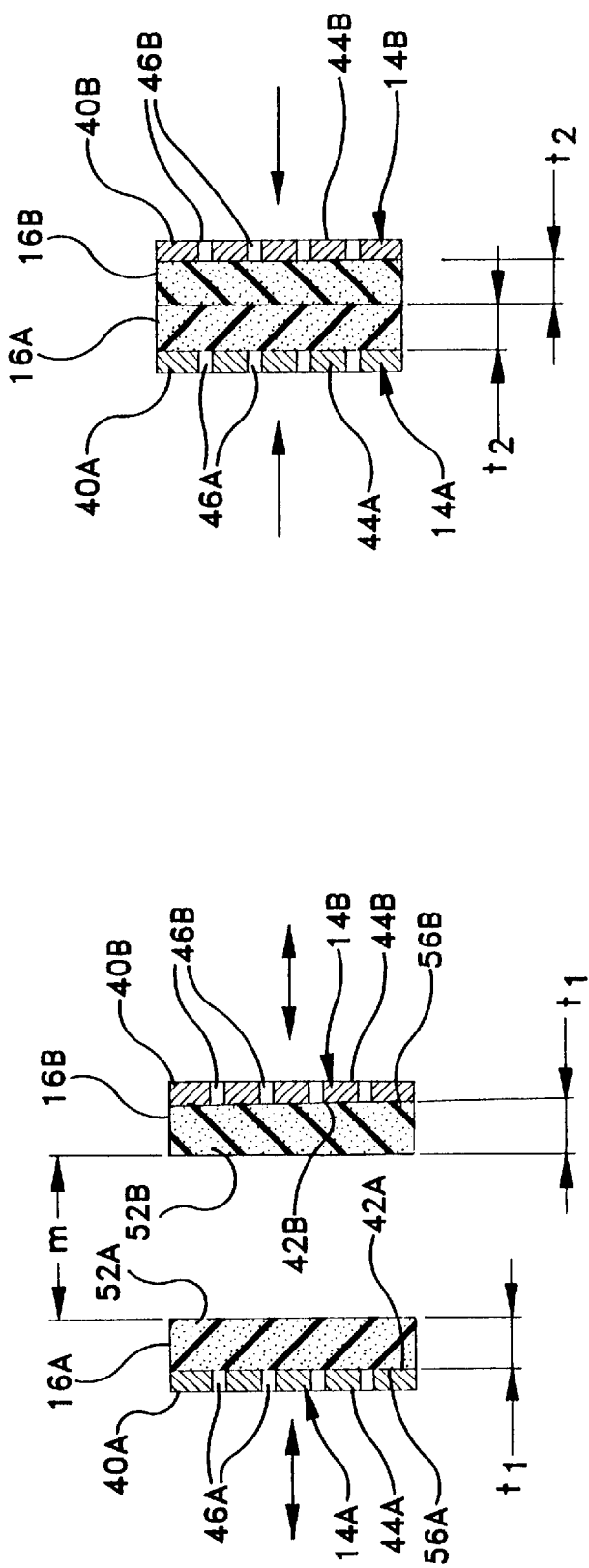

Members 14A, 14B have a movement sequence schematically illustrated in FIGS. 2A to 2E including an initial rest position with resilient pads 16A, 16B spaced apart a distance "m" from each other. The movement sequence then includes a coating loading position where resilient pads 16A, 16B are in physical contact and have a degree of compression with each other. The degree of compression is determined by comparing the thickness $t_1$ of pads 16A, 16B in the initial rest position as shown in FIG. 2A to thickness $t_2$ of pads 16A, 16B in FIG. 2B showing the coating loading position. The compression of the pads serves to spread the coating onto pads 16A, 16B. The movement sequence then includes movement to an intermediate rest position where resilient pads are again spaced apart distance "m" as shown in FIG. 2C, allowing placement of the object to be coated between the pads. The compression of the pads in the coating loading step followed by the release of the compression in the intermediate rest position serves to load the coating onto the pads and also to distribute it. The movement sequence then includes a coating delivery position where pads 16A, 16B are in physical contact with each other and the object being coated. In the coating delivery position, the pads have a thickness $t_3$ and a degree of compression with each other and the object being coated as represented in FIG. 2D. The degree of compression is determined by comparing the ratio of pad thickness $t_3$ with $t_1$. In the coating delivery position the coating is transferred from pads 16A, 16B to the object.

Preferably, the degree of compression of pads 16A, 16B in the coating loading position ($t_2/t_1$) is greater than the degree of compression in the coating delivery position ($t_3/t_1$). When the degree of compression for coating delivery is less than the degree of compression for coating loading, results show more uniform and precise transfer of the coating to the objects being coated.

Preferably, coating supply system 24 includes a reservoir 26 for holding a coating 27 and a transport system 28A, 28B transporting the coating to the pads through holes 46A, 46B. Each of the preferred reciprocating members 14A, 14B include drive mechanisms 30A, 30B for reciprocal movement of the pads through the movement sequence. Preferably apparatus 10 includes an object placement system 34 for placing objects 12 between the pads and then removing the objects. Preferred apparatus 10 includes a control system 32 for controlling the coating supply system, the reciprocating member drive system and the object placing system.

The preferred coating supply system includes having coating transport system 28A, 28B in fluid communication with second sides 44A, 44B of the backing plates 40A, 40B so that a relatively constant supply of coating is maintained at holes 46A, 46B at back sides 56A, 56B of the foam layers 48A, 48B to load the resilient foam layers.

Control system 32 preferably adjusts coating supply system 28A, 28B so that there is a sufficient amount of coating available for delivery to the object. The control system may be electromechanical, digital and the like to control the coating delivery, the movement of the reciprocating members and the object placement and removal.

A suitable material for the porous foam layer is a reticulated polyurethane foam with between about 300 to about 1250 pores per square centimeter. In applications where the object to be coated is a medical device such a catheter or a hypodermic needle, a preferred foam is a polyurethane foam which has been permanently thermally sintered from an as-blown height of between about 5 cm to 25 cm to a height of about 2.5 cm. One skilled in the art of polymeric foams recognizes that the thermal sintering is also described as "felting," and further described as "firmness" or "firmness ratio" of between 2 and 10. Thermal sintering involves compressing the foam from the as-blown thickness to a desired thickness, and then heated.

When the compression is then released, the foam retains the compressed thickness. This sintering has the effect of increasing the density of the foam by reducing the void volume of the pores in the foam.

In the preferred present apparatus, where the object being coated is a medical device such as a catheter, hypodermic needle, a catheter mounted over a hypodermic needle and the like, preferred resilient foam pads 16A, 16B have a thickness $t_1$ between about 0.25 cm to about 2.5 cm and most preferably between about 0.4 cm to about 0.8 cm. Preferably the object being coated is placed substantially centrally between the resilient foam pads so that when the pads are in the coating delivery position, the object is not substantially deflected. The positioning of the object is particularly important when the object being coated is pointed, e.g. a hypodermic needle or a catheter mounted over a needle. If a pointed object is deflected during the coating delivery compression, there may be a tendency to cause the point to partially imbed in one pad or the other, potentially damaging the point, reducing the service life of the pad and generating undesireable particles.

Preferably the foam has about 10 to about 100 pores per linear cm with a firmness about 4. This preferred foam will have about 85% to about 90% void volume or open pore space. Suitable reticulated polyurethane foams, which are available in a range of firmness between 2 and 10, are available as "Foamex SIF felt" from Speciality Polyurethane, 1500 E. Second Street, Eddystone, Pa. 19013 and from E. E. Murray Co., 707 Umatilla Street, Denver, Colo. 80204. Other foams having similar properties are expected to perform satisfactorily. In cases where the objects to be coated are not medical devices such as needles, blades, catheters and the like, foams having different properties may be desired. In the preferred coating system, the coating is a lubricant. The apparatus of the invention is suitable for application of other coatings including, but not limited to, colorants, pesticides and the like.

For these other applications, foams having different properties and composition may be selected and are included in the scope of the invention.

In the preferred application, the degree of compression between resilient pads 16A, 16B in the coating loading position is greater than the degree of compression in the coating delivery position. These compression positions have the effect of reducing the void volume or open space within the foam When the compression is released from the coating loading position, the foam returns to the original uncompressed volume, and the change in void volume is occupied by the coating charge. When the foam having a charge of coating is compressed into the coating delivery position, the foam preferably substantially engulfs the object being coated, the coating in a portion of the void volume is displaced and transferred to the object being coated.

One skilled in the art of lubricating medical devices recognizes that a coating of polydimethyl siloxane is often used as a lubricant on medical devices such as hypodermic needles, scalpels and guidewires made from metal and on medical devices formed from polymeric materials such as catheters and probes. The purpose of the lubricant coating is to reduce the sliding friction between the device and tissue or the sliding friction between one component of the device and another. In almost all applications of silicone lubricant to medical devices there are two conflicting requirements governing the amount applied; there should be some uniform minimum amount applied over the entire surface where the sliding friction is to be reduced; and there should not be excess or visible silicone present on the device. These requirements are often in conflict with each other since polydimethyl siloxane with viscosity above about 500 cs applied by direct dipping into the neat material, while providing complete coverage, generally results in an undesirable excess which leads to visible droplet formation. Currently, many silicone lubricant applications rely on use of a volatile solvent carrier to dilute the silicone, insure complete coverage of the object and avoid deposition of excess lubricant.

Since polydimethyl siloxane is non-polar, many solvents otherwise suitable for its delivery are quite flammable and the medical device industry evolved toward non-flammable chlorofluorocarbon solvents. With the recent recognition of the ozone depletion problem any of these solvent based dilution systems are no longer practical.

Figure 3:
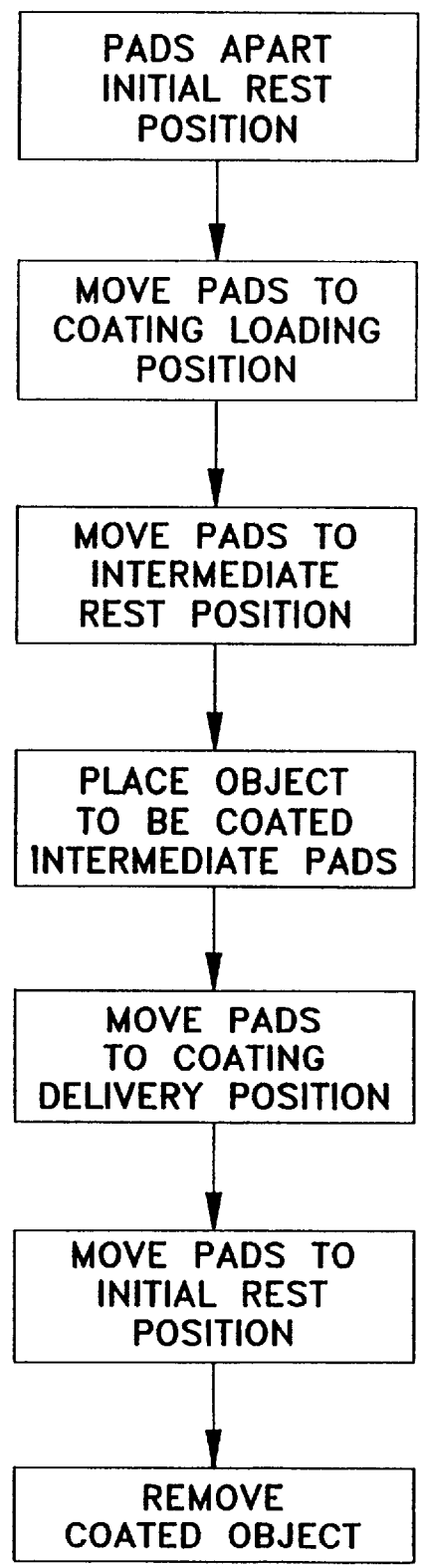
FIG. 3 is a flow chart for a method of applying coating to an object with the apparatus illustrated in FIG. 1.

As an example, data is presented related to coating four 14 gauge catheters at a time with 12,500 cs. polydimethyl siloxane using the preferred embodiment of the present invention illustrated in FIGS. 1—3. The control used in this study was standard commercial product having identical components that was lubricated with identical silicone applied using a chlorofluorocarbon solvent based application system. This example is not to be considered limitative of the invention to the 14 g catheters, rather it is intended to show the utility and repeatability of the apparatus and method in use over a 24 hour period. In this example, the foam used was firmness 4 polyurethane Foamex. Preferably, pads 16A, 16B are each divided into four sections 17A, 17B, the sections being mounted on each reciprocating member to facilitate easy replacement. Each section 17A, 17B is about 0.635 cm thick ($t_1$) by 1.27 cm wide by 6.35 cm long giving an uncompressed 16A, 16B volume of 41 $cm^3$. The preferred apparatus was set up so that in the coating loading position pads 16A, 16B were compressed to a thickness of 0.158 cm ($t_2$), a 75% compression ($t_2/t_1$ =0.25). In the coating delivery position, the pads 16A, 16B were compressed to a thickness of 0.312 cm ($t_3$), a 50% compression ($t_3/t_1$ =0.5). The void volume, i.e., the pores, in the uncompressed state of the foam is about 88% of 41 $cm^3$. When the foam is under 75% compression, the void volume decreases from 88% to a value of 76%. When the foam returns to the uncompressed state the increase in void volume is 12% of 41 $cm^3$ or 4.92 $cm^3$ which is filled by the preferred coating material, polydimethyl siloxane having a viscosity of 12,500 cs. While the preferred polydimethyl siloxane has a viscosity about 12,500 cs, the present invention is suitable for application of polydimethyl siloxanes or other coatings with Brookfield viscosities at 25° C. between about 10 cs to about 1,000,000 cs.

The 24 hour trial run of the apparatus of the present invention was conducted to apply 12,500 cs polydimethyl siloxane for lubrication to the 14 g peripheral venous catheters mounted over needles. Samples of the coated catheters were taken at regular intervals and the amount of silicone lubricant present on their surface was determined by extraction. In the preferred configuration used in the trial, the reciprocating members are mounted so that the pads are vertical with the motion toward and away from each other being horizontal. Preferably, top surfaces 19A, 19B of the resilient pads are sealed so that when the pads are in the compressed state the coating cannot pass through the top surface of the pad and pool on surfaces 19A, 19B of the pads. The top surface may be sealed by adhesive, fusing by heat, ultrasound and the like. Preferably top surfaces 19A, 19B are fused by pressing against a smooth surfaced heated above the melting point of the polyurethane foam forming a skin.

The results show that the preferred apparatus of the present invention was able to reliably and repeatedly apply 0.30+0.075 mg polydimethyl siloxane to more than 20,000 catheters over a 24 hour period. Comparisons between these experimental catheters lubricated by the preferred apparatus of the present invention and standard commercial product lubricated by application of the same silicone in chlorofluorocarbon solvent show generally similar behavior in standard laboratory performance testing for penetration force and drag force.

A constant concern in manufacture of over needle catheters is damage to the point of the needle during lubrication of the catheter and introduction of foreign matter onto the catheter or needle point during lubrication. In the trial, there was overall comparable performance of the catheters lubricated by the preferred present invention to standard commercial product indicating that the lubrication levels were comparable and that the was no detectable degradation in needle point quality. Careful microscopic examination showed that there was little evidence of introduction of particulates resulting from the contact between the resilient foam and the catheter. Further, there was no additional microbial background contamination or bioburden on catheters lubricated in the trial of the preferred apparatus when compared to the standard commercial product.

Referring now to FIGS. 4–12, alternative embodiments of the coating apparatus of the present invention are illustrated. In these embodiments the coating loading and the coating delivery include compression and release of a porous resilient member being loaded with and delivering coating to an object. Accordingly, substantially similar components performing substantially similar functions will be numbered identically to those components of the embodiment of FIGS. 1–3 except that the reference characters will include hundreds digits to identify those components in FIGS. 4–12.

Figure 4:
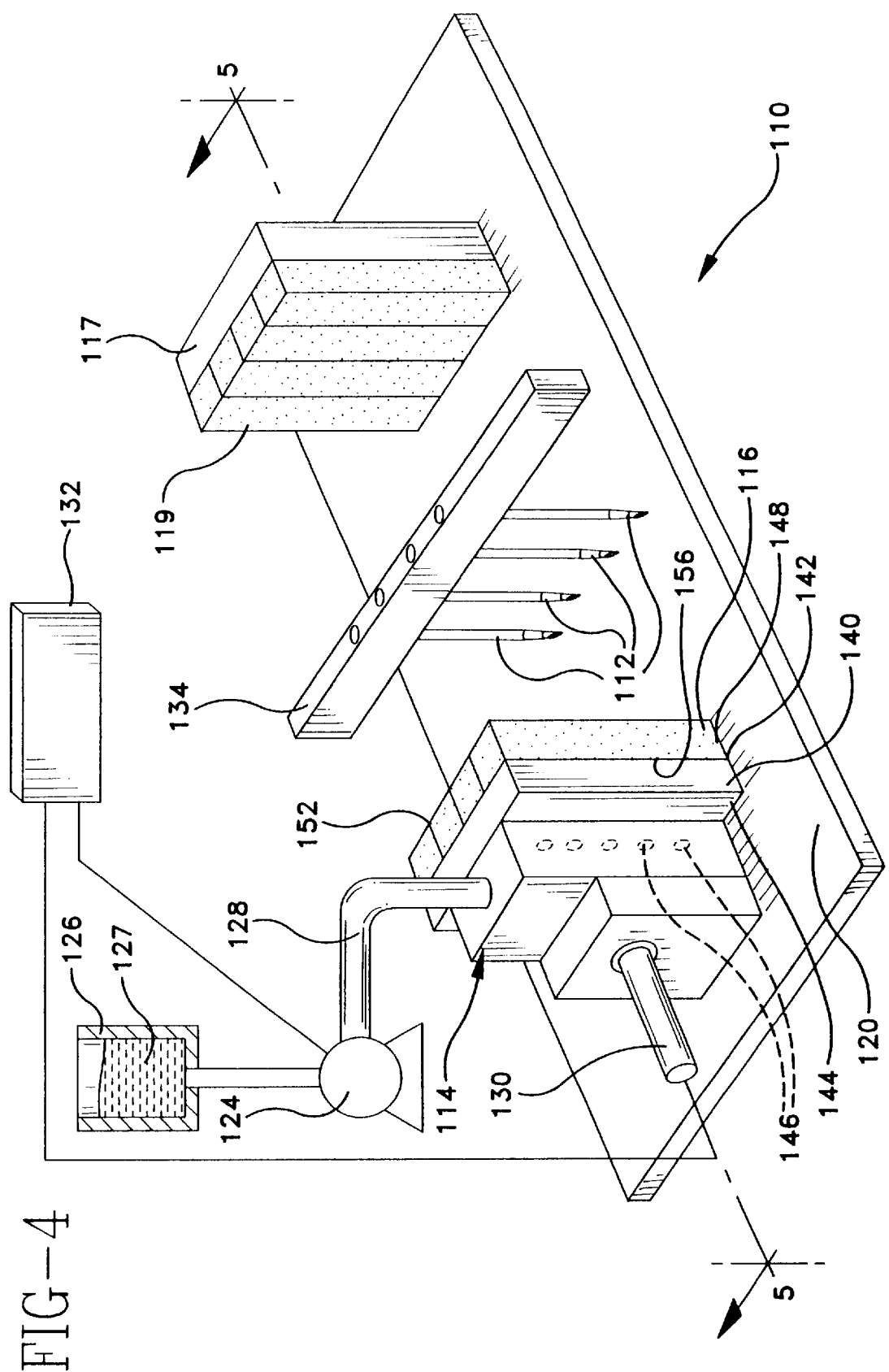
FIG. 4 is a perspective partially sectioned view of another embodiment of the apparatus of the present invention.
Figure 5A:
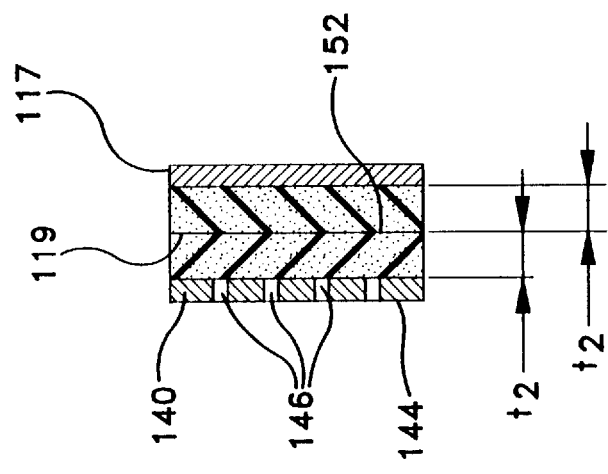
Figure 5B:
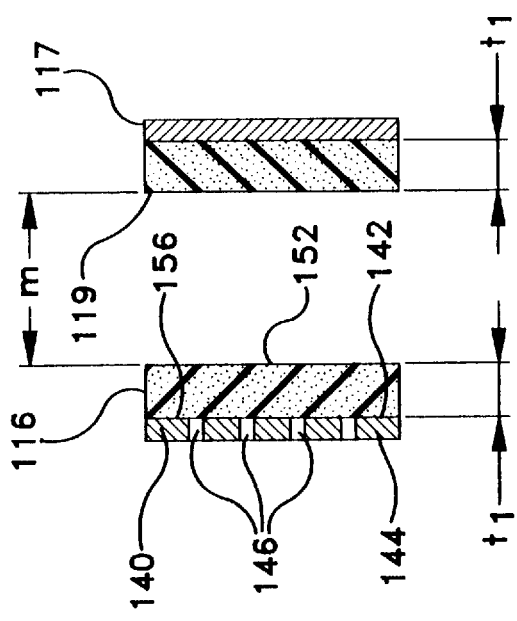

In the embodiment illustrated in FIGS. 4–6, apparatus 110 includes a reciprocating member 114 with a coating supply system 124 for supplying a coating to a resilient pad 116. Preferably resilient pad 116 includes a backing plate 140 having a first side 142 and a second side 144 and having a plurality of holes 146 therethrough. Pad 116 further preferably includes a reticulated resilient foam layer 148 having a front side 152 and a back side 156. Back side 156 is preferably fixedly attached to first side 142 of the backing plate.

Member 114 has sequential movement positions, illustrated in FIGS. 5A to 5E, similar to that described for the embodiment of FIGS. 1–3. In the embodiment of FIGS. 4–6, coating 127 is supplied to resilient pad 116 by a coating supply system 124 from a coating reservoir 126 through a coating transport system 128. In the movement sequence, member 114 includes an initial rest position with resilient pad 116 spaced a distance "m" from a fixed member 117 having a resilient surface 119. The movement sequence then includes a coating loading position with resilient pad 116 in physical contact with and having a degree of compression with the fixed member as shown by comparing the thickness $t_1$ of pad 116 in the initial rest position shown in FIG. 5A to thickness $t_2$ of pad 116 in FIG. 5B which shows the coating loading position. The compression serves to load and spread the coating into pad 116. The sequential movement then includes movement to an intermediate rest position shown in FIG. 5C, where resilient pad 116 is again spaced a distance "m" away from fixed member 117. The intermediate rest position allows placement of object 112 to be coated between resilient pad 116 and fixed member 117. The movement sequence then includes a coating delivery position shown in FIG. 5D where pad 116 is in physical contact with and has a degree of compression with surface 119 of the fixed member and the object to be coated. The coating delivery position serves to transfer the coating from pad 116 to the object. Preferably, object 112 is placed closely adjacent to surface 119 of the fixed member so that object 112 is not substantially deflected by the physical contact of pad 116 in the coating delivery position.

Preferably, the degree of compression of pad 116 in the coating loading position ($t_2/t_1$) is greater than the degree of compression in the coating delivery position ($t_3/t_1$). In this embodiment, coating supply system 124 having coating reservoir 126 and a coating transport system 128 perform similar functions as in the embodiment of FIGS. 1–3 as does object delivery system 134. Reciprocating member 114 preferably is mounted on a base 120 and includes a drive mechanism 130. Apparatus 110 preferably includes a control system 132 to synchronize movement of reciprocating member 114, movement of objects 112 and delivery of the coating so that the amount of coating delivered to the object is precisely controlled.

A preferred method for applying a coating to an object using apparatus 110 is outlined in FIG. 6. The method includes having pad 116 away from fixed surface 117 in an initial rest position, moving the pad to a coating loading position against fixed surface 117 and moving the pad away from the fixed surface so that an object to be coated may be moved to a position intermediate to the pad and the fixed surface. The preferred method then includes moving the pad to a coating delivery position where the pad is in physical contact and in a degree of compression with the object and the fixed surface applying the coating to the object. The pad is then moved away from the fixed surface and the coated object removed.

Figure 7:
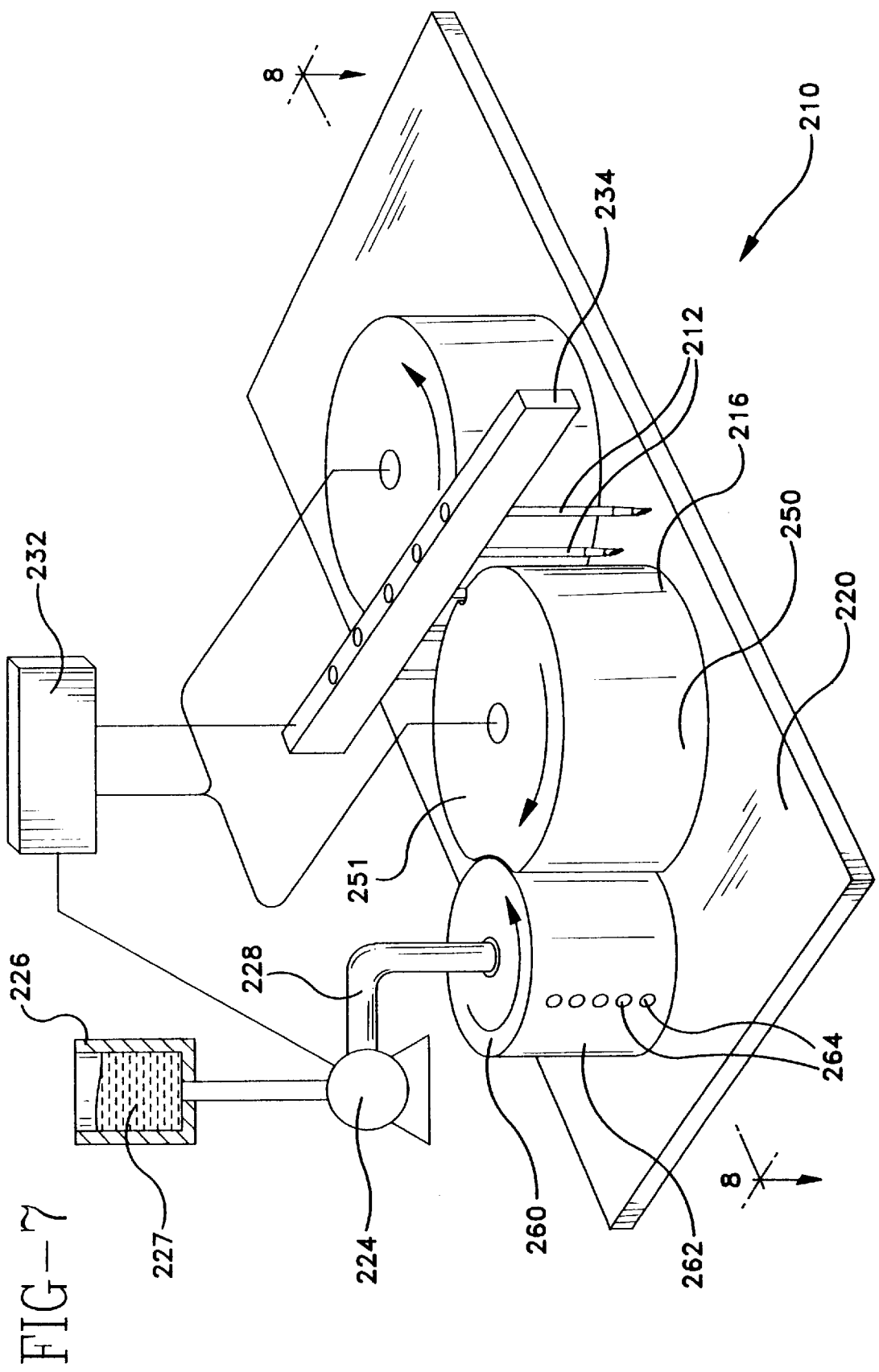
FIG. 7 is a perspective view of another embodiment of the apparatus of the present invention.
Figure 8:
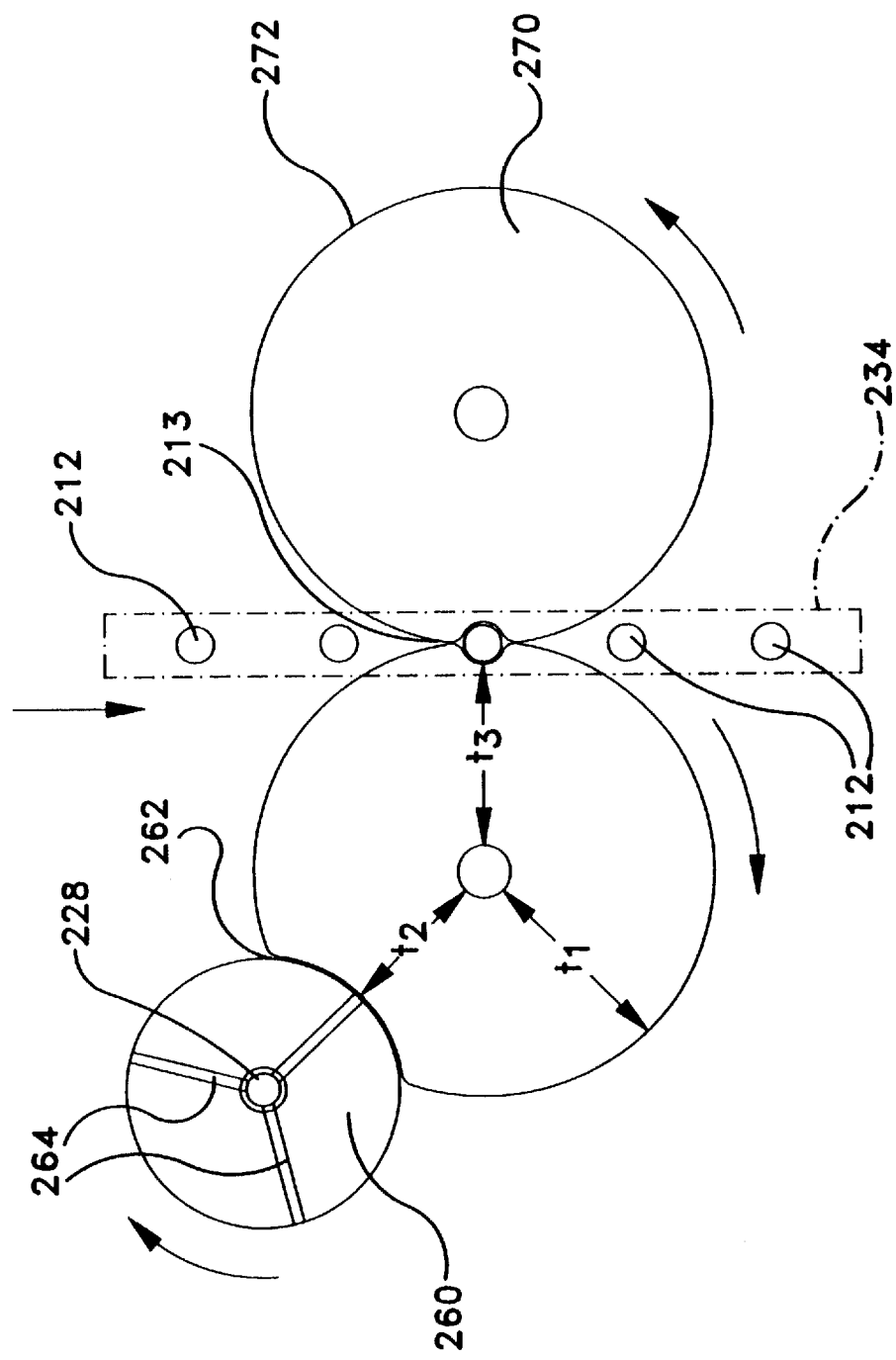
FIG. 8 is a partial cross-sectional schematic view of the apparatus of FIG. 7 along the line 8—8.
Figure 9:
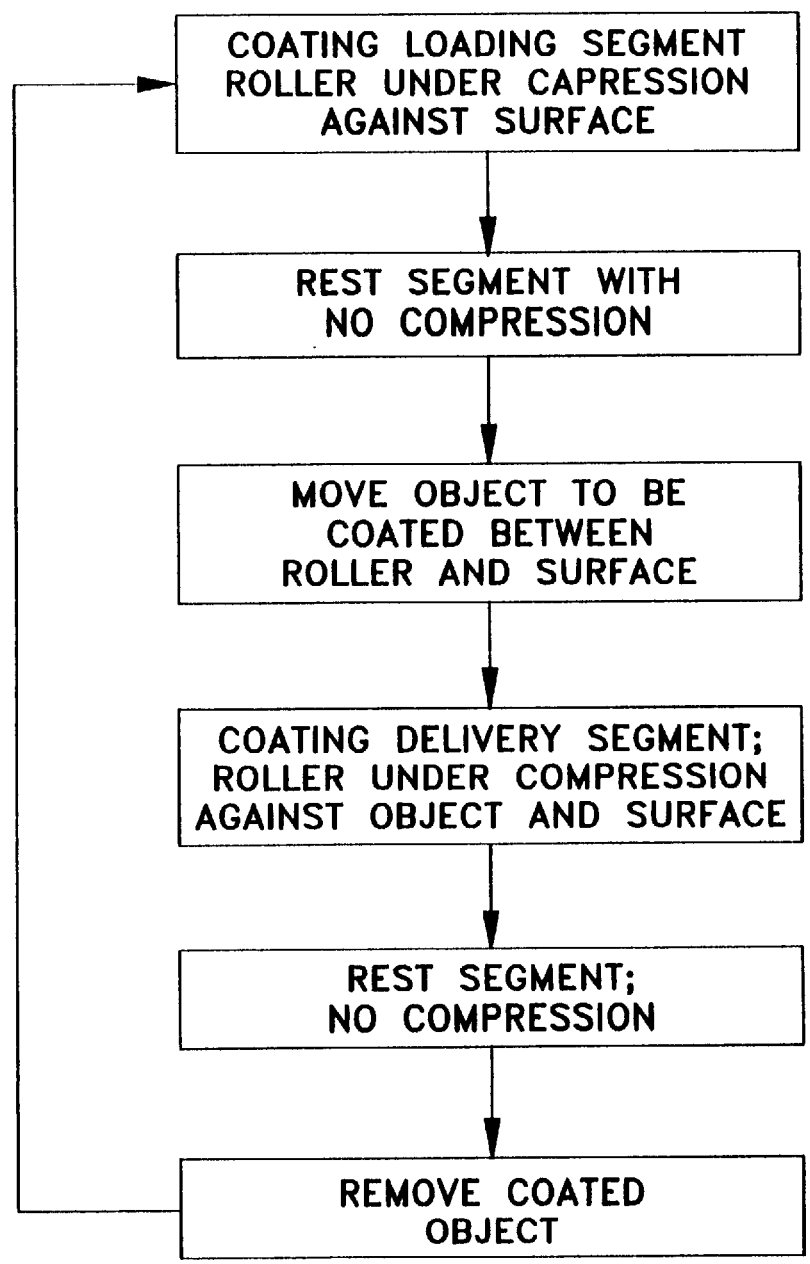
FIG. 9 is a flow chart for a method of applying coating to an object with the apparatus of FIG. 7.

Other embodiments illustrated in FIGS. 7–12, are within the scope of the present invention. As shown in FIGS. 7–9, an apparatus 210 is used for coating an object 212. Apparatus 210 includes a rotating member 250 with a porous resilient roll 216. Rotating member 250 rotates about a shaft 251. Rotating member 250 has a rotary movement sequence schematically illustrated in FIG. 8. The movement sequence includes a coating loading segment where resilient roll 216 is in physical contact with and has a degree of compression with a coating loading member 260. The coating loading member 260 preferably is supplied with coating by a coating supply system 224 which includes a coating reservoir 226 with a coating 227 and a coating transport system 228. The coating loading member may rotate counter to the rotation of rotating member 250 or it may be fixed, but preferably, coating loading member 260 rotates counter to member 250. Member 260 preferably is porous with the coating being supplied to a contact surface 262 of member 260 through a plurality passageways 264 supplied by transport system 228. As resilient roll 216 passes surface 262, the degree of compression may be determined by comparing uncompressed thickness $t_1$ with thickness $t_2$ where roll 216 contacts coating member 260. The $t_2/t_1$ compression serves to transfer the coating to the resilient roll and spread it uniformly.

Apparatus 210 preferably further includes a base 220 and a rotating support member 270 having a resilient surface 272. As resilient roll 216 rotates past coating loading member 260 the compression is released and roll 216 returns to uncompressed thickness $t_1$. Apparatus 210 preferably includes an object handling system 234 for moving objects 212 to be coated between resilient roll 216 and rotating support member 270 at the coating loading segment so that resilient roll 216 is in physical contact and has a degree of compression with object 212 and surface 272 of the rotating support member in an area 213. The compression between roll 216 and object 212 transfers the coating to the object. The degree of compression between resilient roll 216 and surface 272 is shown by thickness ($t_3/t_1$). Preferably the degree of compression in the coating loading segment is greater than the degree of compression in the coating delivery segment.

A method for applying a coating to an object using the apparatus 210 of the present invention includes moving objects 212 between rotating member 250 which has porous resilient roll 216 with a loading of a coating mounted for rotatory motion about shaft 251 in a coating delivery segment so that the roll contacts resilient surface 272 on rotating support member 270 and object 212 with a degree of compression.

Figure 10:
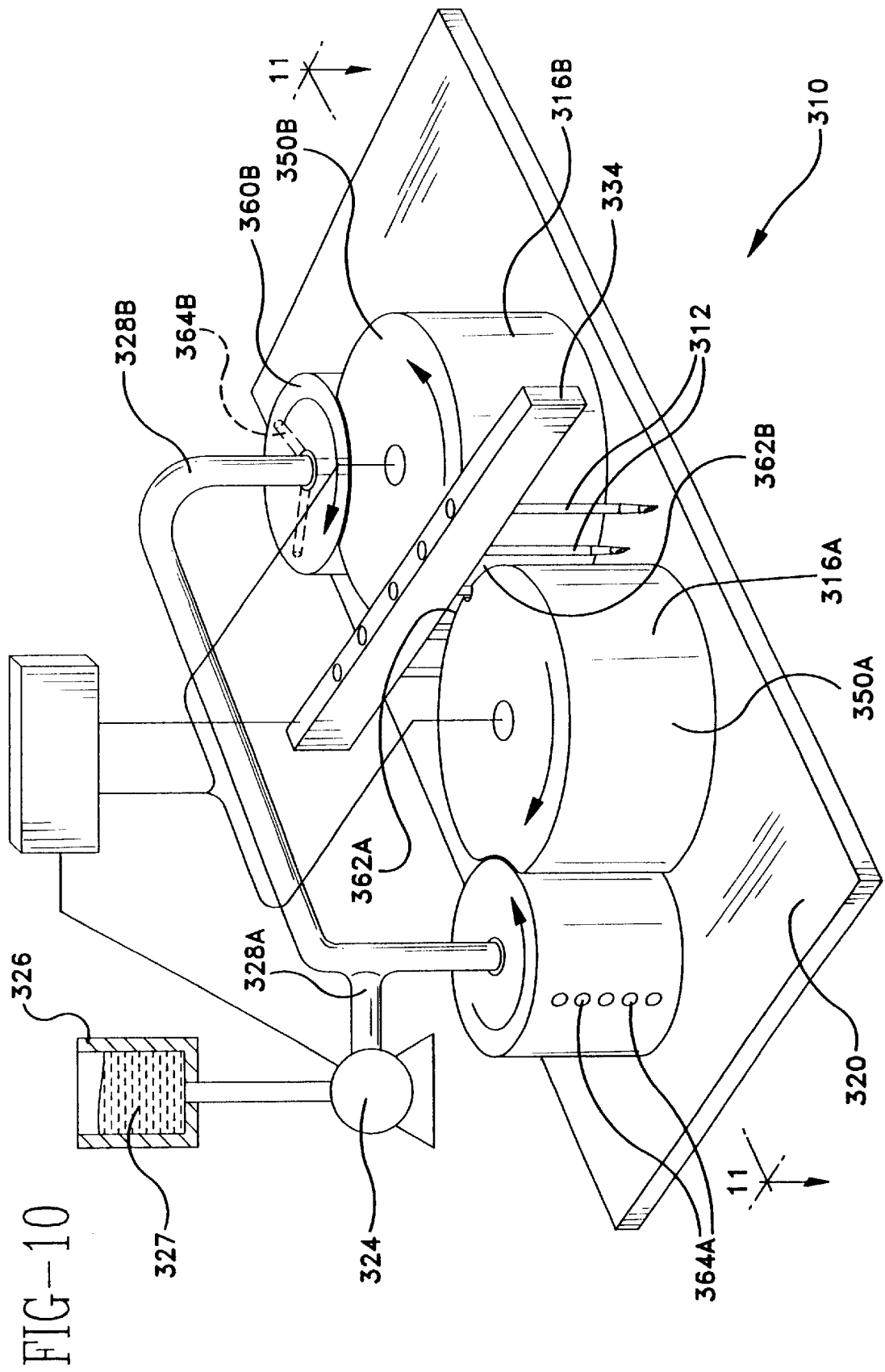
FIG. 10 is a perspective view of a further embodiment of the apparatus of the present invention.
Figure 11:
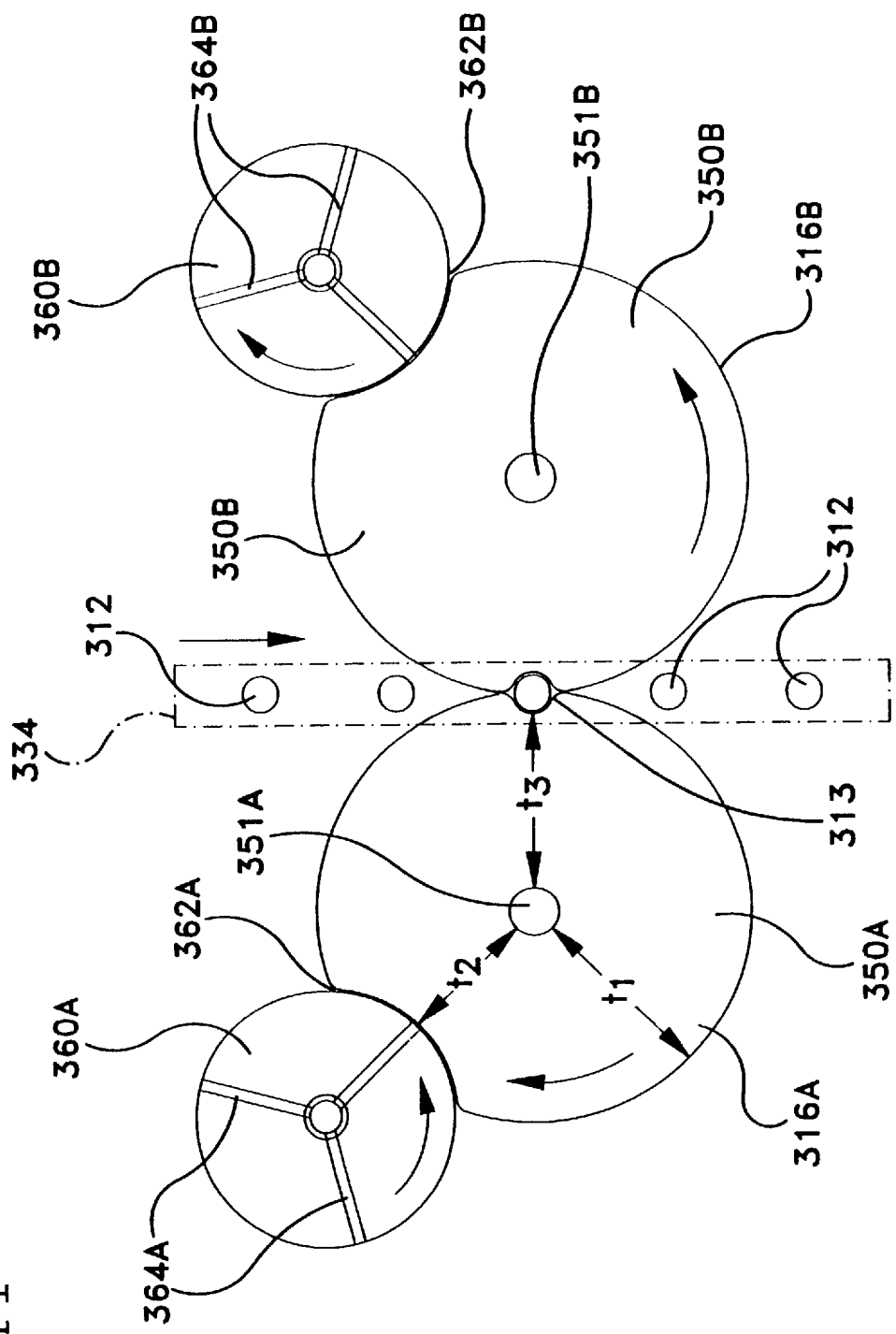
FIG. 11 is a partial schematic view of the apparatus of FIG. 10 along the line 11—11.
Figure 12:
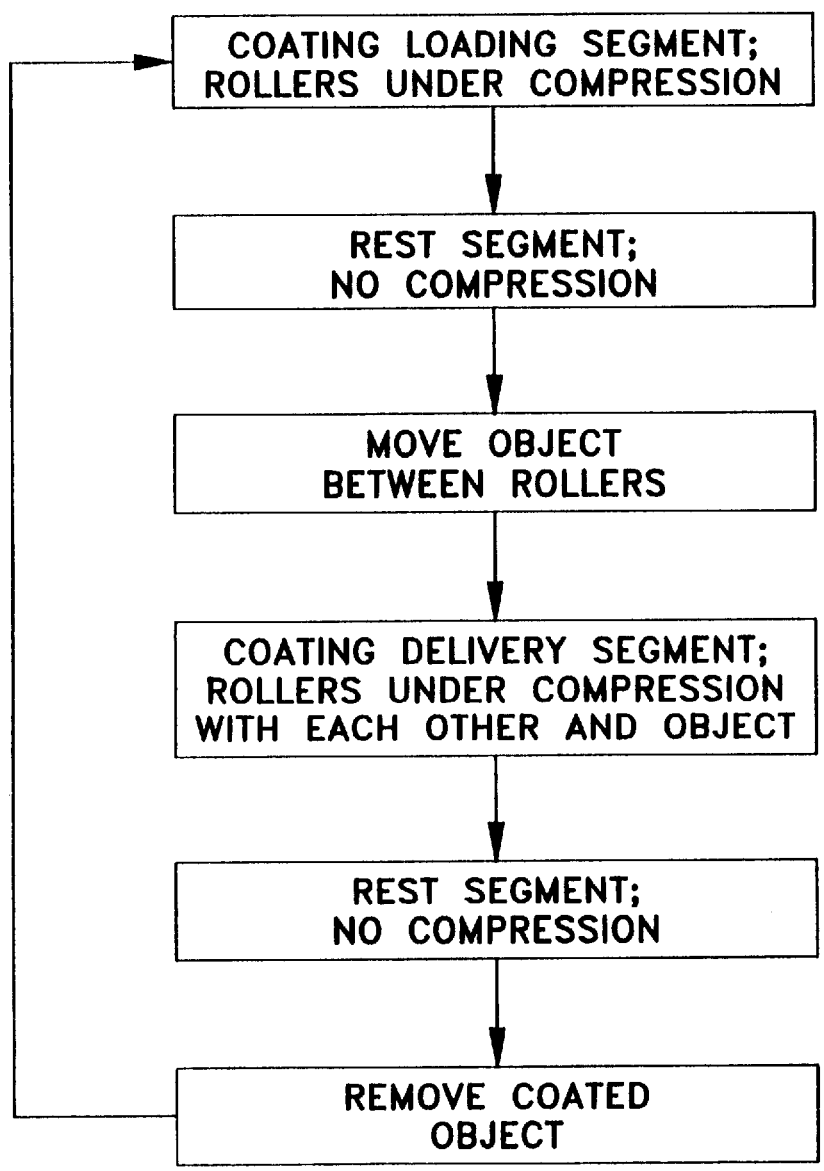
FIG. 12 is a flow chart for a method of applying coating to an object with the apparatus of FIG. 10.

As shown in FIGS. 10–11, an apparatus 310 for applying a coating to an object 312 includes a pair of rotating members 350A, 350B mounted for counter-rotatory movement so that the members contact each other during one segment of the movement in an area of contact 313 and do not contact each other at other segments of the movement. Rotating members 350A, 350B rotate respectively about shafts 351A, 351B. Rotating members 350A, 350B have a rotary movement sequence schematically illustrated in FIG. 11. The movement sequence includes a coating loading segment where each resilient roll 316A, 316B is respectively in physical contact and has a degree of compression with coating loading members 360A, 360B. Coating loading members 360A, 360B may rotate counter to the rotation of rotating member 350A, 350B or the coating loading members may be fixed, but preferably, coating loading members 360A, 360B rotate counter to members 350A, 350B. Members 360A, 360B preferably are porous with the coating being supplied to contact surfaces 362A, 362B through a plurality of passageways 364A, 364B supplied by transport system 328A, 328B. As resilient rolls 316A, 316B, respectively, pass surfaces 362A, 362B, the degree of compression may be determined by comparing uncompressed thickness $t_1$ with thickness $t_2$ where rolls 316A, 316B contact coating members 360A, 360B. The compression $t_2/t_1$ serves to transfer the coating to the resilient rolls and spread it uniformly into the rolls.

Apparatus 310 preferably further includes a base 320 for mounting the rotating members and the coating loading members. As resilient rolls 316A, 316B rotate past coating loading members 360A, 360B, the compression is released and rolls 316A, 316B return to the uncompressed thickness $t_1$. Apparatus 310 preferably includes an object handling system 334 for moving objects 312 to be coated between the resilient rolls 316A, 316B in the direction of rotation of the rolls at the position where the rolls are in physical contact with each other and have a degree of compression. This movement of the objects between the rolls causes the rolls to have a degree of compression with object 312 being coated transferring coating from the rolls to the object. Preferably, the movement of objects 312 between resilient rolls 316A, 316B is a continuous motion into and out of area of contact 313 of the rolls. The degree of compression between the resilient rolls is determined by thickness $t_3/t_1$. Preferably the degree of compression in the coating loading ($t_2/t_1$) segment is greater than the degree of compression ($t_3/t_1$) in the coating delivery segment.

A method for applying a coating to an object using the apparatus 310 of the present invention includes moving the object 312 between rotating members 350A, 350B which has porous resilient rolls 316A, 316B with a loading of a coating. The rolls are mounted for counter rotatory motion about shafts 351A, 351B in a coating delivery segment so that the rolls contact each other and the object being coated with a degree of compression.

The coating apparatus of the present invention may be compactly built to fit on assembly machines into space currently used for solvent based coating apparatus. The apparatus and method for its use demonstrate a capability to produce product having similar quality and performance properties to standard commercial product produced with solvent based coating. The apparatus of the present invention is also compatible with the assembly rate requirements and efficiency of current assembly machines using solvent based coating systems. The present invention provides a simple and reliable coating station for medical device assembly machines allowing manufacturers to eliminate the use of solvent based coating systems in many applications.

What is claimed is:

1. A method for applying a coating to an object, comprising:

providing a first roller having a first porous resilient pad thereon with an unbiased thickness $t_1$;

rotating the first roller;

rotating a first coating roller with a plurality of holes therein in counter rotary motion with respect to the first roller so that the first coating roller engages the first roller and compresses the first porous resilient pad in an area of engagement to a thickness $t_2$;

supplying a coating material to the first coating roller;

transferring the coating material from the first coating roller to the first porous resilient pad via the plurality of holes in the first coating roller;

moving an object into engagement with the first roller so the object compresses the first porous resilient pad in an area of engagement to a thickness $t_3$ wherein $t_1$ is greater than $t_3$ and $t_3$ is greater than $t_2$; and transferring the coating material from the first porous resilient pad to the object.

2. The method of claim 1 further comprising:

providing a second roller having a second porous resilient pad thereon in opposed relation to the first roller to define an interface therebetween;

rotating the second roller;

rotating a second coating roller with a plurality of holes therein in counter rotary motion with respect to the second roller so that the second roller engages the second roller and compresses the porous resilient pad;

supplying a coating material to the second coating roller;

transferring the coating material from the second coating roller to the second porous resilient pad via the plurality of holes in the second coating roller; and transferring the coating material from the second porous resilient pad to the object.

3. The method of claim 2 wherein the object is moved into the interface between the first roller and the second roller so the object engages and compresses the first porous resilient pad and the second porous resilient pad.

4. The method of any of claims 1–3, wherein the first porous resilient pad is a reticulated polyurethane foam.

5. The method of claim 4 wherein the first porous resilient pad has between about 300 and about 1250 pores per square centimeter.

6. The method of any of claims 1–3 wherein the first porous resilient pad has an unbiased thickness $t_1$ of between about 0.25 cm to about 2.5 cm.

7. The method of claim 6, wherein the first porous resilient pad is a reticulated polyurethane foam.

8. The method of claim 7 wherein the first porous resilient pad has between about 300 and about 1250 pores per square centimeter.

* * * * *